(12) United States Patent
Yeh et al.

(10) Patent No.: US 9,044,467 B2
(45) Date of Patent: *Jun. 2, 2015

(54) METHODS FOR ASSISTING ANTI-CANCER DRUGS

(75) Inventors: Wen-Li Yeh, Tainan (TW); Chun-Chih Huang, Tainan (TW)

(73) Assignee: NEW BELLUS ENTERPRISES CO., LTD., Tainan (TW)

( * ) Notice: Subject to any disclaimer, the term of this patent is extended or adjusted under 35 U.S.C. 154(b) by 138 days.

This patent is subject to a terminal disclaimer.

(21) Appl. No.: 13/594,569

(22) Filed: Aug. 24, 2012

(65) Prior Publication Data

US 2013/0089534 A1  Apr. 11, 2013

(30) Foreign Application Priority Data

Oct. 11, 2011 (TW) .............................. 100136826 A

(51) Int. Cl.
*A61K 35/00* (2006.01)
*A61K 38/44* (2006.01)
*A61K 36/07* (2006.01)

(52) U.S. Cl.
CPC ................. *A61K 38/44* (2013.01); *A61K 36/07* (2013.01); *A61K 2236/19* (2013.01)

(58) Field of Classification Search
None
See application file for complete search history.

(56) References Cited

U.S. PATENT DOCUMENTS

| | | | |
|---|---|---|---|
| 6,391,615 B1 * | 5/2002 | Huang et al. | 435/254.1 |
| 2009/0143280 A1 * | 6/2009 | Kristiansen | 514/8 |
| 2009/0196885 A1 * | 8/2009 | Yao et al. | 424/195.15 |

OTHER PUBLICATIONS

Chan et al., The statins as anticancer agents, 2003, Clinical Cancer Research 9(1): 10-19.*
Kanda, Naoki, et al. "STAT3 is constitutively activated and supports cell survival in association with survivin expression in gastric cancer cells." Oncogene 23.28 (2004): 4921-4929.*
Meireles et al., Filtration of a bacterial fermentation broth: harvest conditions effects on cake hydraulic resistance, 2003, Bioprocess and Biosystems Engineering 25(5): 309-314.*
Lu et al., Protective effects of mycelia of <i> Antrodia camphorata and Armillariella tabescens in submerged culture against ethanol-induced hepatic toxicity in rats, 2007, Journal of Ethnopharmacology 110(1): 160-164.*

* cited by examiner

*Primary Examiner* — Robert Yamasaki
(74) *Attorney, Agent, or Firm* — Hannah M. Tien

(57) ABSTRACT

A method for assisting an anti-cancer drug comprising administrating an effective amount of *Antrodia camphorata* fermentation solution to improve life quality of patient suffering from cancers after chemotherapy is provided.

8 Claims, 2 Drawing Sheets

Figure 1

The culture of the selected *Antrodia Camphorata* mycelia in a 2 L culture bottle (30°C, 100 rpm, 8-10 days)

↓

The scale-up culture in fermenting tank (2 L→200 L, 30°C, 50 rpm, 0.5 vvm, 3-5 days)

↓

The scale-up culture in fermenting tank (200 L→5000 L, 30°C, 30 rpm, 0.5 vvm, 8-10 days)

↓

Centrifugation (7400 rpm) and separation

↓

*Antrodia Camphorata* fermentation solution

↓

Concentration by the membrane filtering (3000 MW) under low temperature

↓

Concentration solution

↓

Sterilization

↓

Sterile stuffing under low temperature

↓

Packing

↓

Quality check

↓

Storage

↓

Shipment

METHODS FOR ASSISTING ANTI-CANCER DRUGS

FIELD OF THE INVENTION

The present invention is related to a method for assisting an anti-cancer drug. Particularly, the present invention is related to a method for improving the life quality of patient suffering from cancers after chemotherapy comprising administration of *Antrodia camphorata* fermentation solution to the patients.

BACKGROUND OF THE INVENTION

*Antrodia camphorata* (Niu Chang-Zhi) is also called "Chang-Zhi", "Niu Chang-Ku", "Red-Chang", "Red Chang-Chih", "Chang-Ku", camphor chamber mushroom and so on, which is an endemic species in Taiwan growing on the inner rotten heart wood wall of *Cinnamomum kanehirae* Hay in the altitude of 450 M to 2000 M in the mountains of Taiwan. Because the growth rate of natural *Antrodia camphorata* is extremely slow, and its growth season is from June to October, therefore the price of *Antrodia camphorata* is very expensive. In addition, the demand of *Antrodia camphorata* is still high due to their biologically active components having potential pharmaceutical value.

In traditional Taiwanese medicine, the curative effects of *Antrodia camphorata* include removing rheumatism, smoothing vitality, nourishing blood, eliminating bruises, benefiting spleen and stomach, lessening accumulation, detoxification, subsiding swelling, sedation and relieving pain, and is used as a great antidote for detoxifying food poisoning, diarrhea, vomiting and pesticide poisoning. Furthermore, it has adjuvant therapeutic effects on liver and stomach dysfunction and the diseases of blood circulation. *Antrodia camphorata*, like general edible and medicinal mushrooms, is rich in numerous nutrients including polysaccharides (such as-glucosan), triterpenoids, superoxide dismutase (SOD), adenosine, proteins (immunoglobulins), vitamins (such as vitamin B, nicotinic acid), trace elements (such as calcium, phosphorus and germanium and so on), nucleic acid, agglutinin, amino acids, steroids, lignins and blood pressure stabilizers (such as antrodia acid) and the like. These bioactive ingredients are believed to exhibit beneficial effects such as: anti-tumor, immunity enhancement, anti-allergy, inhibition of platelet agglutination, anti-virus, anti-bacteria, anti-hypertension, blood glucose-lowering, cholesterol-lowering, hepatic protection and the like.

Recently, many compounds identified in *Antrodia camphorata* are demonstrated to exhibit anti-cancer activities. The 4,7-dimethoxy-5-methyl-1,3-benzodioxole purified from dry fruiting body of *Antrodia camphorata* can inhibit the proliferation of human colon epithelial cells. In addition, 24-methylenelanosta-7,9-(11)-diene-3β,15[alpha]-diol-21-oic (MMH01), another compound identified in *Antrodia camphorata* mycelium, is shown to inhibit the growth of human leukemia cancer cells (U937) and pancreatic cancer cells (BxPC3). Aside from their anti-cancer activities, some compounds isolated from *Antrodia camphorata* have also displayed anti-inflammatory activities. The 5 different compounds have been purified from *Antrodia camphorata* which include antroquinonol B, 4-acetyl-antroquinonol B, 2,3-(methylenedioxy)-6-methyl benzene-1,4-diol, 2,4-dimethoxy-6-methyl-benzene-1,3-diol and antrodin D, and found that they can efficiently inhibit NO production and exhibit certain anti-inflammatory effects.

Beside *Antrodia camphorata* is reported to have the above mentioned effects from the previously published experimental results, the method of the present invention is used for assisting an anti-cancer drug to improve the life quality of patient suffering from cancers.

BRIEF DESCRIPTION OF THE DRAWINGS

FIG. 1 shows the preparation process of *Antrodia camphorata* fermentation solution.

SUMMARY OF THE INVENTION

Figure 2:
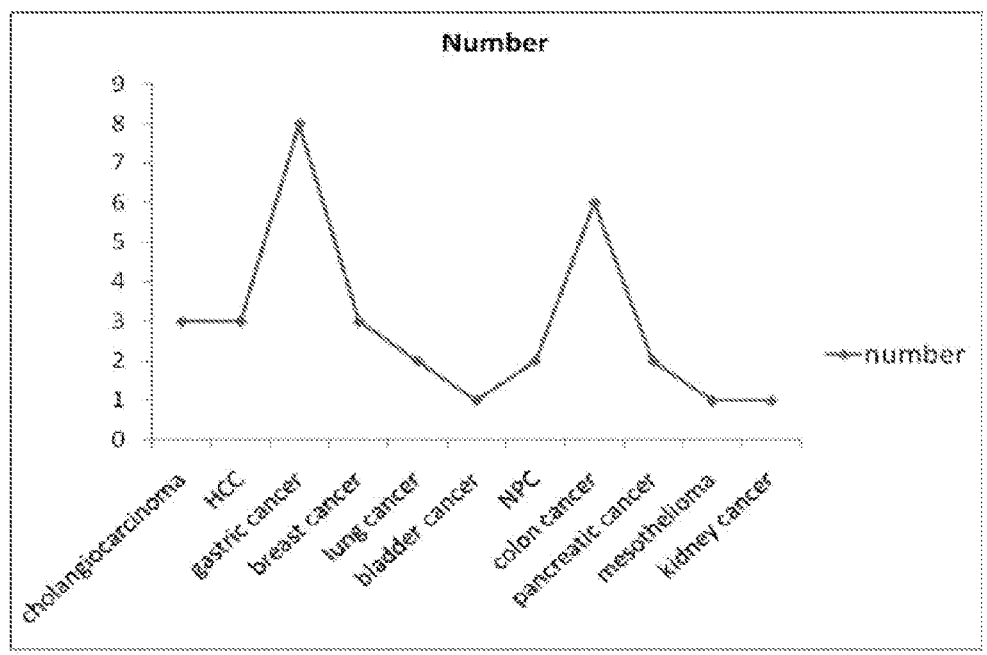
FIG. 2 shows the patient numbers of enrolling each type of cancer. HCC: hepatocellular carcinoma; NPC: nasopharyngeal carcinoma.

The present invention is directed to a method for assisting an anti-cancer drug comprising administrating an effective amount of *Antrodia camphorata* fermentation solution to a patient in need thereof. The *Antrodia camphorata* fermentation solution comprises polysaccharides, triterpenoids, γ-aminobutyric acid or superxide dismutase.

Detailed Description of the Invention

The present invention is directed to a method for assisting an anti-cancer drug in a patient in need thereof comprising administrating an effective amount of *Antrodia camphorata* fermentation solution to the patient. The *Antrodia camphorata* fermentation solution comprises polysaccharides, triterpenoids, γ-aminobutyric acid or superxide dismutase. In a preferred embodiment, the *Antrodia camphorata* fermentation solution is *Antrodia camphorata* mycelium fermentation solution. The *Antrodia camphorata* fermentation solution or *Antrodia camphorata* mycelium fermentation solution are membrane filtered. The *Antrodia camphorata* fermentation solution is useful for the patient suffering from at least one type of cancer, such as but not limited to gastric cancer, breast cancer, cholangiocarcinoma, nasopharyngeal carcinoma, colon cancer, pancreatic cancer, lung adenocarcinoma or liver cancer, and the gastric cancer is preferred.

In one embodiment, the administration of the present *Antrodia camphorata* fermentation solution is accompanied with at least one anti-cancer drug to the patient in need thereof after chemotherapy. The method of the present invention is to increase the number of monocytes or basophiles in the patient, to decrease the amount of bilirubin or blood platelets in the patient, or to improve the patient's life quality during cancer therapy. The improvement of life quality comprises reducing pain, fatigue, and negative emotions, and increasing physical activity or physical activity level of the patient in need thereof.

EXAMPLES

Example 1

Preparation of *Antrodia Camphorata* Fermentation Solution

As shown in FIG. 1, the selected *Antrodia Camphorata* mycelium was inoculated into a 2 L culture bottle and cultured with an agitation rate of 100 rpm at 30° C. for 8-10 days. The whole colony was then scale-up cultured in a 200 L fermenting tank under agitated at 50 rpm, with an aeration of 0.5 vvm at 30° C. for 3-5 days. Finally, it was scale-up cultured in a 5000 L fermenting tank under agitated at 30 rpm, with an aeration of 0.5 vvm at 30° C. for 8-10 days. The cultured mycelia were centrifuged at 7400 rpm and then were concentrated by low-temperature membrane filtering (3000 MW). After blending and sterilization, the concentrated solution was filled into containers in sterile condition under low temperature to form the final product. Every 20 mL of *Antrodia camphorata* fermentation solution contained 2100 mg polysaccharides, 172 mg triterpenoids, and 2687.5 mg γ-aminobutyric acid.

Technical Characteristics of Preparation:

Various kinds of active ingredient and secondary fermentation-metabolite with bioactivity were fully remained by using of computational automatic control equipments, low-temperature membrane filtering, and sterile filling process under low temperature. The final product completely retained the original aromatic flavor and the effects of special components from *Antrodia camphorata*.

Example 2

The Requirements for Enrolling Patients (1) Patients suffering from cancer between 18~80 years of age.
(2) According to the method established by the American Eastern Cooperative Oncology Group (ECOG), patients whose score of performance status was between 0-2 (score "0" means fully normal activity, and score "2" means ambulatory and capable of self-care but unable to carry out any work activities, up and about more than 50% of working hours).
(3) Patients without significant abnormality in liver and kidney functions [total bilirubin≤1.5×UNL, serum glutamic-oxaloacetic transaminase (SGOT/AST)≤3-5×UNL, serum glutamic pyruvate transaminase (SGPT/ATL)≤3-5×UNL, Creatinine<1.5 mg/dL or Estimated creatinine clearance≥60 mL/min].
(4) Patient's estimated life expectancy is longer than 12 weeks.
(5) Patients treated with but poor tolerance to platinum-based or anthracycline-based regimen.

Example 3

Grouping of the Patients

Patients suffering from cancers receiving conventional chemotherapy were recruited through out-patient clinic or ward of oncology and hematology. After completion of informed consent, the patients were divided into two groups by randomized, double-blinded clinical trial: control group treated with chemotherapy and placebo, and test group treated with chemotherapy and the present *Antrodia camphorata* fermentation solution.

Example 4

Data Collection

The patients received the treatment of placebo or *Antrodia camphorata* fermentation solution in the interval of chemotherapies. 20 mL of placebo or *Antrodia camphorata* fermentation solution (Amon Biotech Co., Ltd.) were given to the patients twice a day (once in the morning and once at night-time) for 30 days. The blood test and questionnaire survey were performed at the day of 0 (V0), 7 (V1), and 30 (V2) after receiving treatment.

Example 5

Experimental Items

Blood samples were harvested before, during, and after the therapeutic regiment. The therapeutic effect was predicted and evaluated by analysis of tumor markers, biochemistry and blood test, and questionnaire such as life function status questionnaire (ECOG performance status scale), quality of life questionnaire (EORTC QLQ-C30) and fatigue questionnaire (MFI-20). At the same time, the ability of *Antrodia camphorata* to increase life expectancy, alleviate side effect, and improve life quality, and the effect of chemotherapy related toxicity were assayed.

Example 6

Statistical Analysis

1. Average Survival Time:
   The relative risk and 95% confidence interval of average survival time between these two groups were calculated by Kaplan-Meier test and two tailed Log rank test.
2. Evaluation of Quality of Life:
   Analysis of variance (ANOVA) was used for statistical validation of the differences between these two groups.
3. Number of Side Effect:
   The differences between these two groups were compared by Fisher's event test or time to event analyses.
4. The continuous variable was compared by Mann-Whitney U test.

Example 7

The Analytical Results of the First Phase

When receiving the test drug prior to conventional drug, the patients of the test group were susceptible to gastrointestinal symptoms, such as hyperacidity and diarrhea. These symptoms could be eliminated by changing the order of drug administration.

Example 8

The Analytical Results of the Secondary Phase

1. The patient numbers of enrolling each type of cancer was shown in FIG. 2.
2. Results of Intention-to-Treat (ITT) blood analysis:
   There was no significant difference between the test group and the control group for the pre-test value V0. For ANOVA test of post-test value V2, the amounts of AST and ALT of the test group were higher than that of the control group (AST: $p=0.041$, ALT: $p=0.033$; see Table 1).

TABLE 1

Compare of V0 and V2 between the control group and test group (ANOVA test)

|  | Test group (n = 19) (mean ± SD) | Control group (n = 13) (mean ± SD) | P value |
|---|---|---|---|
| V0 |  |  |  |
| Number of Sex (%) |  |  | 0.513 |
| Male | 11 (42.1%) | 6 (53.8%) |  |
| Female | 8 (57.9%) | 7 (46.2%) |  |
| Age (year) | 54.68 ± 11.76 | 52.77 ± 13.47 | 0.673 |
| BUN | 14.63 ± 6.22 | 16.00 ± 6.19 | 0.558 |
| Creatinine | 0.88 ± 0.34 | 0.81 ± 0.26 | 0.527 |
| ALK-P | 163.53 ± 114.38 | 128.31 ± 115.73 | 0.401 |
| SGOT/AST | 38.79 ± 22.73 | 27.93 ± 12.36 | 0.092 |
| SGPT/ALT | 29.00 ± 16.88 | 20.00 ± 12.85 | 0.115 |
| Bilirubin | 0.62 ± 0.23 | 0.49 ± 0.17 | 0.114 |
| Hemoglobin | 10.83 ± 1.61 | 11.95 ± 1.97 | 0.086 |

TABLE 1-continued

Compare of V0 and V2 between the control group and test group (ANOVA test)

|  | Test group (n = 19) (mean ± SD) | Control group (n = 13) (mean ± SD) | P value |
|---|---|---|---|
| Hematocrit | 32.79 ± 4.65 | 35.77 ± 5.75 | 0.117 |
| RBC | 3.62 ± 0.53 | 3.93 ± 0.66 | 0.149 |
| WBC | 6.85 ± 3.50 | 5.80 ± 3.80 | 0.428 |
| Lymphocytes | 18.04 ± 13.29 | 17.99 ± 8.86 | 0.990 |
| Monocytes | 5.53 ± 4.30 | 4.52 ± 2.95 | 0.436 |
| Eosinophils | 1.38 ± 1.62 | 0.83 ± 0.98 | 0.284 |
| Basophils | 0.26 ± 0.36 | 0.21 ± 0.24 | 0.666 |
| Platelet | 197.00 ± 85.39 | 201.62 ± 81.51 | 0.879 |
| ESR | 46.24 ± 31.91 | 38.33 ± 15.01 | 0.492 |
| V2 | | | |
| Number of Sex (%) | | | 0.513 |
| Male | 11 (42.1%) | 6 (53.8%) | |
| Female | 8 (57.9%) | 7 (46.2%) | |
| Age (year) | 54.68 ± 11.76 | 52.77 ± 13.47 | 0.673 |
| BUN | 17.87 ± 7.11 | 17.00 ± 7.16 | 0.762 |
| Creatinine | 0.87 ± 0.35 | 0.85 ± 0.25 | 0.818 |
| ALK-P | 130.15 ± 106.67 | 106.58 ± 69.61 | 0.503 |
| SGOT/AST | 41.79 ± 26.79 | 26.92 ± 11.31 | 0.041 |
| SGPT/ALT | 29.74 ± 16.39 | 19.00 ± 10.81 | 0.033 |
| Bilirubin | 0.80 ± 0.75 | 0.61 ± 0.33 | 0.404 |
| Hemoglobin | 10.70 ± 2.20 | 11.59 ± 1.35 | 0.203 |
| Hematocrit | 32.30 ± 6.11 | 34.77 ± 4.33 | 0.218 |
| RBC | 3.52 ± 0.66 | 3.75 ± 0.37 | 0.264 |
| WBC | 6.74 ± 3.45 | 5.48 ± 2.04 | 0.246 |
| Lymphocytes | 22.83 ± 12.58 | 19.94 ± 10.68 | 0.504 |
| Monocytes | 7.98 ± 3.42 | 7.69 ± 3.54 | 0.820 |
| Eosinophils | 1.07 ± 1.23 | 1.34 ± 1.51 | 0.589 |
| Basophils | 0.20 ± 0.18 | 0.37 ± 0.36 | 0.124 |
| Platelet | 155.53 ± 67.51 | 205.46 ± 82.37 | 0.070 |
| ESR | 42.14 ± 30.45 | 47.27 ± 24.46 | 0.654 |

SD: standard deviation; BUN: blood urea nitrogen; ALK-P: alkaline phosphatase; RBC: red blood cell; WBC: white blood cell; ESR: erythrocyte sedimentation rate 3. Compare of the pre- and post-test value between the control group and test group As shown in Table 2, the amount of alkaline phosphatase (ALK-P) was significantly decreased and the amount of monocytes were significantly increased in the test group (paired-t-test; ALK-P: p=0.015; monocytes: p=0.002). As shown in Table 3, it demonstrated the significant increase of ALK-P and the significant decrease of monocytes by Wilcoxon Signed Rank Test (ALK-P: p=0.019; monocytes: p=0.003). These results suggested that the physical function of the patients in the test group was better than that of the control group.

TABLE 2

Compare of the pre- and post-test value between the control group and test group (paired-t-test)

| | The difference of pair | | | | | | | |
|---|---|---|---|---|---|---|---|---|
| | | | | 95% confidence interval | | | | |
| | | | The mean | | | | | |
| | Mean | SD | of SD | Lower | Upper | T | df | P value |
| BUN | −1.087 | 6.809 | 1.42 | −4.031 | 1.857 | −0.766 | 22 | 0.452 |
| Creatinine | −0.01406 | 0.16603 | 0.02935 | −0.07392 | 0.0458 | −0.479 | 31 | 0.635 |
| ALK-P | 30.651 | 65.916 | 11.839 | 6.472 | 54.829 | 2.589 | 30 | 0.015 |
| SGOT/AST | −1.375 | 11.845 | 2.094 | −5.646 | 2.896 | −0.657 | 31 | 0.516 |
| SGPT/ALT | −0.031 | 12.993 | 2.297 | −4.716 | 4.653 | −0.014 | 31 | 0.989 |
| Bilirubin | −0.1531 | 0.5507 | 0.0973 | −0.3517 | 0.0454 | −1.573 | 31 | 0.126 |
| Hemoglobin | 0.2219 | 1.355 | 0.2395 | −0.2666 | 0.7104 | 0.926 | 31 | 0.361 |
| Hematocrit | 0.7031 | 4.1965 | 0.7418 | −0.8099 | 2.2161 | 0.948 | 31 | 0.351 |
| RBC | 0.12969 | 0.49322 | 0.08719 | −0.04814 | 0.30751 | 1.487 | 31 | 0.147 |
| WBC | 0.1938 | 3.1486 | 0.5566 | −0.9414 | 1.3289 | 0.348 | 31 | 0.730 |
| Lymphocytes | −3.6375 | 11.5367 | 2.0394 | −7.7969 | 0.5219 | −1.784 | 31 | 0.084 |
| Monocytes | −2.7469 | 4.5781 | 0.8093 | −4.3974 | −1.0963 | −3.394 | 31 | 0.002 |
| Eosinophils | −0.025 | 1.4939 | 0.2641 | −0.5636 | 0.5136 | −0.095 | 31 | 0.925 |
| Basophils | −0.0281 | 0.2715 | 0.048 | −0.126 | 0.0698 | −0.586 | 31 | 0.562 |
| Platelet | 23.063 | 81.934 | 14.484 | −6.478 | 52.603 | 1.592 | 31 | 0.121 |
| ESR | −2.524 | 16.928 | 3.694 | −10.229 | 5.182 | −0.683 | 20 | 0.502 | df: the degree of freedom

TABLE 3

Compare of the pre- and post-test value between the control group and test group (Wilcoxon Signed Rank Test)

| | BUN | Creatinine | ALK-P | SGOT/AST | SGPT/ALT | Bilirubin | Hemoglobin | Hematocrit |
|---|---|---|---|---|---|---|---|---|
| Z vale | −0.872(a) | −0.584(a) | −2.345(b) | −1.108(a) | −0.216(a) | −1.207(a) | −0.720(b) | −0.716(b) |
| P value | 0.383 | 0.559 | 0.019 | 0.268 | 0.829 | 0.227 | 0.471 | 0.474 |

TABLE 3-continued

Compare of the pre- and post-test value between the control group and test group (Wilcoxon Signed Rank Test)

|         | RBC        | WBC        | Lymphocytes | Monocytes | Eosinophils | Basophils  | Platelet   | ESR        |
|---------|------------|------------|-------------|-----------|-------------|------------|------------|------------|
| Z value | −1.608(b)  | −0.195(a)  | −1.431(a)   | −3.02(a)  | −0.312(b)   | −0.852(a)  | −1.608(b)  | −0.488(a)  |
| P value | 0.108      | 0.845      | 0.153       | 0.003     | 0.755       | 0.394      | 0.108      | 0.626      |

(a): according to negative rank;
(b): according to positive rank

4. Compare between the pre- and post-test value of the test group

As shown in Table 4, the pre-test values of ALK-P and blood platelet were both higher than the post-test values, which indicated the decrease of the values. On the contrary, the pre-test value of monocytes was higher than the post-test value, which indicated the increase of the value (Wilcoxon Signed Rank Test; ALK-P: p=0.018; blood platelet: p=0.049; monocytes: p=0.049).

TABLE 4

Comparative between the pre- and post-test value of the test group (Wilcoxon Signed Rank Test)

|         | BUN        | Creatinine | ALK-P      | SGOT/AST   | SGPT/ALT   | Bilirubin  | Hemoglobin | Hematocrit |
|---------|------------|------------|------------|------------|------------|------------|------------|------------|
| Z value | −0.714(a)  | −0.166(a)  | −2.356(b)  | −1.046(a)  | −0.242(a)  | −1.013(a)  | −0.02(b)   | −0.022(a)  |
| P value | 0.475      | 0.868      | 0.018      | 0.295      | 0.809      | 0.311      | 0.984      | 0.983      |

|         | RBC        | WBC        | Lymphocytes | Monocytes | Eosinophils | Basophils  | Platelet   | ESR        |
|---------|------------|------------|-------------|-----------|-------------|------------|------------|------------|
| Z value | −0.805(b)  | −0.616(a)  | −1.569(a)   | −1.972(a) | −0.663(b)   | −0.646(b)  | −1.972(b)  | −0.701(b)  |
| P value | 0.421      | 0.538      | 0.117       | 0.049     | 0.507       | 0.518      | 0.049      | 0.483      |

(a): according to negative rank;
(b): according to positive rank

5. The analytic results of Quality of life questionnaire (EORTC QLQ-C30C)

As shown in Table 5, the V2 score of the test group was lower than that of the control group in the activity aspects (long-distance walk, work or daily activities, and leisure activities), pain and emotions by using of Mann-Whitney U test. The higher score represented more serious condition.

TABLE 5

Analysis of EORTC QLQ-C30 (Mann-Whitney U test)

| V2 | Mean rank of the test group | Mean rank of the control group | P value |
|---|---|---|---|
| Physical function | | | |
| Whether you find it diffcult to walk a long distance | 13.63 | 20.69 | 0.028 |
| Social function | | | |
| Whether you feel restricted on working or daily activity | 13.50 | 20.88 | 0.009 |
| Whether you feel restricted on preference or leisure activity | 13.50 | 20.88 | 0.009 |
| The symptom that cancer patient often suffered | | | |
| Have you ever feel pain | 13.53 | 20.85 | 0.014 |
| Do you need rest | 13.58 | 20.77 | 0.023 |
| Emotional function | | | |
| Are you feel irascibility | 13.82 | 20.42 | 0.029 |

6. Analytic results of ECOG performance status

The post-test value (V2) was analyzed by using of Mann-Whitney U test. As shown in Table 6, the mean rank of patients with ECOG 2 score in the test group was lower than that of the control group in the performance status (the test group: 14.00; the control group: 20.15) by the analysis of Mann-Whitney U test. The higher score represented more serious condition.

TABLE 6

Analytic results of EORTC QLQ-C30

| | Mann-Whitney U test | Wilcoxon Signed Rank Test | Z value | P value (two tail) | P value (2 * one tail) |
|---|---|---|---|---|---|
| Normal activity fully ambulatory | 104.000 | 195.000 | −1.481 | 0.139 | 0.472 |
| Able to carry on normal activities; minor signs or symptoms of disease; or normal activity with effort | 96.000 | 187.000 | −1.240 | 0.215 | 0.305 |
| Some bed time, but needs to be in bed less than 50% of normal daytime; able to care for self; unable to carry on normal activity or to do active work | 117.500 | 307.500 | −0.402 | 0.688 | 0.821 |
| Need to be in bed more than 50% of normal daytime; capable of limited selfcare | 76.000 | 266.000 | −2.897 | 0.004 | 0.071 |
| Unable to get out of bed; unable to care for self | 117.000 | 208.000 | −0.827 | 0.408 | 0.821 |

7. Compare between the control group and test group among the patients suffering from gastric cancer As shown in Table 7, the post-test value of basophil was significantly higher than the pre-test value. This suggested that the number of basophil of these two groups were both increased (Wilcoxon Signed Rank Test, basophil: p=0.041)

TABLE 7

Compare between the pre- and post-test value of the test group and control group (Wilcoxon Signed Rank Test)

| | BUN | Creatinine | ALK-P | SGOT/AST | SGPT/ALT | Bilirubin | Hemoglobin | Hematocrit |
|---|---|---|---|---|---|---|---|---|
| Z value | −1.270(a) | −0.676(a) | −0.840(b) | −0.140(b) | −0.169(a) | −0.704(a) | −0.508(a) | −0.280(a) |
| P value | 0.204 | 0.499 | 0.401 | 0.889 | 0.866 | 0.481 | 0.611 | 0.779 |

| | RBC | WBC | Lymphocyte | Monocytes | Eosinophils | Basophils | Platelet | ESR |
|---|---|---|---|---|---|---|---|---|
| Z value | −0.280(b) | −0.676(b) | −1.120(a) | −1.540(a) | −0.524(a) | −2.041(a) | −1.120(b) | −0.772(b) |
| P value | 0.779 | 0.499 | 0.263 | 0.123 | 0.600 | 0.041 | 0.263 | 0.440 |

(a): according to negative rank;
(b): according to positive rank

Example 9

Conclusion

According to the above-mentioned, the *Antrodia camphorata* fermentation solution of the present invention is able to increase the number of monocyte and basophile; decrease the amount of ALK-P and blood platelet; and reduce pain, fatigue and negative emotions; and increase activity period or physical activity level of the patient in need thereof during chemotherapy.

What is claimed is:

1. A method for improving life quality of a patient receiving an anti-cancer drug and suffering from pain, fatigue, negative emotions, decreased activity period and decreased physical activity level due to the anti-cancer drug, comprising administering an effective amount of *Antrodia camphorata* fermentation solution to the patient, wherein (i) the *Antrodia camphorate* fermentation solution comprises polysaccharides, triterpenoids and γ-aminobutyric acid, (ii) the anti-cancer drug is a platinum-based or anthracycline-based anti-cancer drug and (iii) the administering improves the life quality of the patient by reducing said pain, fatigue and negative emotions, and increasing said activity period and physical activity level.

2. The method of claim 1, wherein the cancer is gastric cancer, breast cancer, cholangiocarcinoma, nasopharyngeal carcinoma, colon cancer, pancreatic cancer, lung adenocarcinoma or liver cancer.

3. The method of claim 2, wherein the cancer is gastric cancer.

4. The method of claim 1, wherein the *Antrodia camphorata* fermentation solution is administered accompanying with the anti-cancer drug to the patient.

5. The method of claim 1, wherein the administering increases the number of monocytes or basophiles in the patient, or decreases the amount of alkaline phosphatases or blood platelets in the patient during cancer therapy.

6. The method of claim 1, wherein the *Antrodia camphorata* fermentation solution is *Antrodia camphorata* mycelium fermentation solution.

7. The method of claim 6, wherein the *Antrodia camphorata* mycelium fermentation solution is membrane filtered.

8. The method of claim 1, wherein the *Antrodia camphorata* fermentation solution is membrane filtered.

\* \* \* \* \*